United States Patent [19]

McGee et al.

[11] Patent Number: 5,637,090
[45] Date of Patent: Jun. 10, 1997

[54] MULTIPLE ELECTRODE ELEMENT FOR MAPPING AND ABLATING HEART TISSUE

[75] Inventors: David L. McGee, Palo Alto; Russell A. Houser, Livermore; David K. Swanson, Mountain View, all of Calif.

[73] Assignee: EP Technologies, Inc., Sunnyvale, Calif.

[21] Appl. No.: 655,289

[22] Filed: May 15, 1996

Related U.S. Application Data

[63] Continuation of Ser. No. 531,891, Sep. 22, 1995, abandoned, which is a continuation of Ser. No. 138,235, Oct. 15, 1993, abandoned.

[51] Int. Cl.$^6$ ............................................. A61B 5/04
[52] U.S. Cl. ................................. 604/95; 604/280
[58] Field of Search .................... 604/95, 96, 264, 604/280; 606/32, 33, 41, 46, 45, 48, 49, 50; 128/642; 607/115, 116, 119, 154, 122

[56] References Cited

U.S. PATENT DOCUMENTS

| | | | |
|---|---|---|---|
| 5,239,999 | 8/1993 | Imran | 128/642 |
| 5,275,162 | 1/1994 | Edwards et al. | 128/642 |
| 5,293,868 | 3/1994 | Nardella | 128/642 |
| 5,322,064 | 6/1994 | Lundquist | 128/642 |
| 5,327,889 | 7/1994 | Imran | 128/642 |
| 5,327,905 | 7/1994 | Avitall | 128/642 |
| 5,328,467 | 7/1994 | Edwards et al. | 128/642 |
| 5,357,956 | 10/1994 | Nardella | 128/642 |
| 5,365,926 | 11/1994 | Desai | 128/642 |

*Primary Examiner*—Robert A. Hafer
*Assistant Examiner*—Manuel Mendez
*Attorney, Agent, or Firm*—Ryan, Maki, Mann & Hohenfeldt

[57] ABSTRACT

Systems and methods sense electrical events in heart tissue to identify the location of an arrhythmogenic focus for ablation. The systems and methods establish a contact site between heart tissue and a curvilinear electrode array. The systems and methods monitor signals representing electrical events sensed by the electrodes in the contact site. The signals are displayed as graphic information that represents the time sequence in which the electrodes sense a given electrical event. By moving the electrode array to one or additional contact sites in the general direction of the electrode that first sensed the electrical event, the physician homes in on a contact site in which all electrodes on the array sense the given electrical event at generally the same time. This contact site contains the arrhythmogenic focus. The systems and methods convey ablating energy to bipolar pairs of the electrodes to form large bipolar lesions in heart tissue.

26 Claims, 10 Drawing Sheets

MULTIPLE ELECTRODE ELEMENT FOR MAPPING AND ABLATING HEART TISSUE

This is a continuation of application Ser. No. 08/531,891 filed on Sep. 22, 1995, now abandoned which is Continuation of application Ser. No. 08/138,235 filed Oct. 15, 1993, and now abandoned.

FIELD OF THE INVENTION

The invention relates to systems and methods for mapping and ablating the interior regions of the heart for treating cardiac conditions.

Background of the Invention

Myocardial ventricular tachycardia (MVT) is most commonly associated with re-entrant pathways associated with ischemic or infarcted myocardial regions. Conduction properties in these damaged regions of the heart differ from healthy myocardial tissue, resulting in slow conduction of electrical impulses. Long, convoluted conduction pathways also form at the boundary zones between healthy myocardial tissue and these damaged tissue regions.

MVT can be treated by drugs and implantable cardiovertor defibrillators (ICD's). However, ablating re-entrant pathways can successfully cure MVT.

It is believed that lesions larger than those created by current electrophysiological therapy are needed to more consistently cure MVT of ischemic origins.

Conventional cardiac ablation systems designed to cure re-entrant supra ventricular tachycardia (SVT), often create lesions in myocardial tissue with a penetration depth of about 3 to 5 mm and a lesion volume of less than 0.2 cm$^3$, depending upon the size of the electrode and the amount of power that is applied.

However, to consistently cure MVT by ablation, a penetration depth greater than 3 to 5 mm and a lesion volume of at least 1 cm$^3$ is estimated to be required.

The solution lies in larger electrodes. Yet, larger electrodes themselves pose problems of size and maneuverability that weigh against safe and easy introduction through a vein or artery into the heart.

Furthermore, physicians frequently find it difficult to map and localize a suspected arrhythmogenic focus for ablation. Stable and intimate contact between the myocardial tissue and the mapping electrodes are often difficult to achieve and maintain.

As a result, mapping and ablating of intracardiac tissue using conventional catheter-based techniques are often difficult and time consuming.

A need exists for multiple purpose cardiac mapping and ablation catheters having (i) flexibility and maneuverability that permits safe and easy introduction into the heart; (ii) that, once deployed inside the heart, provide a stable and uniform electrode array for mapping and localization of a suspected arrhythmogenic focus; and (iii) that, once the focus is located, emit energy sufficient to cause permanent, irreversible thermal damage to large regions of myocardial tissue.

SUMMARY OF THE INVENTION

The invention provides improved and "smarter" systems and methods for cardiac mapping and ablation.

One aspect of the invention provides an assembly for sensing electrical events and forming bipolar lesions in heart tissue. The assembly includes a support body for contacting heart tissue. The body has a generally circular shape that peripherally forms an open interior region enclosing a portion of the heart tissue it contacts.

According to this aspect of the invention, the support body carries an array of first electrodes having a first physical dimension. The support body also carries an array of second electrodes having a second physical dimension larger than the first dimension. The second electrodes are mutually grouped on the body in diametrically opposite bipolar pairs across the open interior region.

The array can be selectively operated in two modes, one for sensing and the other for ablating. In the sensing mode, the array conveys signals representing electrical events sensed by both the first and second electrodes when in contact with heart tissue. In the ablating mode, the array conveys ablating energy only to the bipolar pairs of the second electrodes, and not to the first electrodes, to form a bipolar lesion in the heart tissue that is enclosed within the open interior region of the support body.

This aspect of the invention provides a multiple purpose electrode array that makes stable and uniform contact with heart tissue. The electrode array can accurately sense electrical events to identify arrhythmogenic foci. Once identified, the same electrode array can be energized with ablating energy to create lesions that are significantly larger in terms of volume and geometry than conventional approaches provide.

Another aspect of the invention provides "smart" systems and methods for sensing electrical events in heart tissue that display the sensed events in a way that quickly and accurately guides the physician to the location of an arrhythmogenic focus.

This aspect of the invention establishes a contact site between heart tissue and a multiple electrode array. The array has a generally circular shape peripherally forming an open interior region. The array carries electrodes in a spaced apart pattern about the open interior region.

According to this aspect of the invention, the systems and methods monitor signals representing electrical events sensed by the electrodes in the contact site. The systems and methods display the signals as graphic information that represents the time sequence in which the electrodes on the support body sense a given electrical event.

The time sequence can begin when the first one of the electrodes senses the given event. Alternatively, the time sequence can begin based upon a time reference initiated by an external source.

The display that embodies this aspect of the invention can vary. It can includes icons symbolizing the electrodes. It can employ alpha-numeric characters that change according to the time sequence of sensing, or it can include colors that change according to the time sequence of sensing.

In a preferred embodiment, the display shows electrogram recordings made by the electrodes. The display orders the presentation of the electrogram recordings from first to last according to time sequence of sensing.

In a preferred embodiment, the sequence in which the electrodes sense the given electrical event is time gated.

Guided by the display, the physician homes in on the focus by moving the electrode array to one or more additional contact sites in the general direction of the electrode that the display indicates first sensed the electrical event. The physician eventually homes in on a contact site where all electrodes on the array sense the given electrical event at generally the same time. Here is where the focus lies, enclosed within the open interior region of the array.

Ablating energy can then be supplied to the bipolar pairs of the electrodes to form a bipolar lesion within the open interior region of the support body. This ablates the focus.

The invention allows the identified arrhythmogenic focus to be mapped and ablated at one time, without the need to employ a separate ablation probe. The invention provides better tissue/electrode contact and stability, to minimize the occurrence of ineffective applications of ablating energy. Furthermore, the invention provides lesions of enlarged size.

The invention thereby provides shorter and more effective procedures, with greater incidence of curative lesions.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENT

Figure 1:
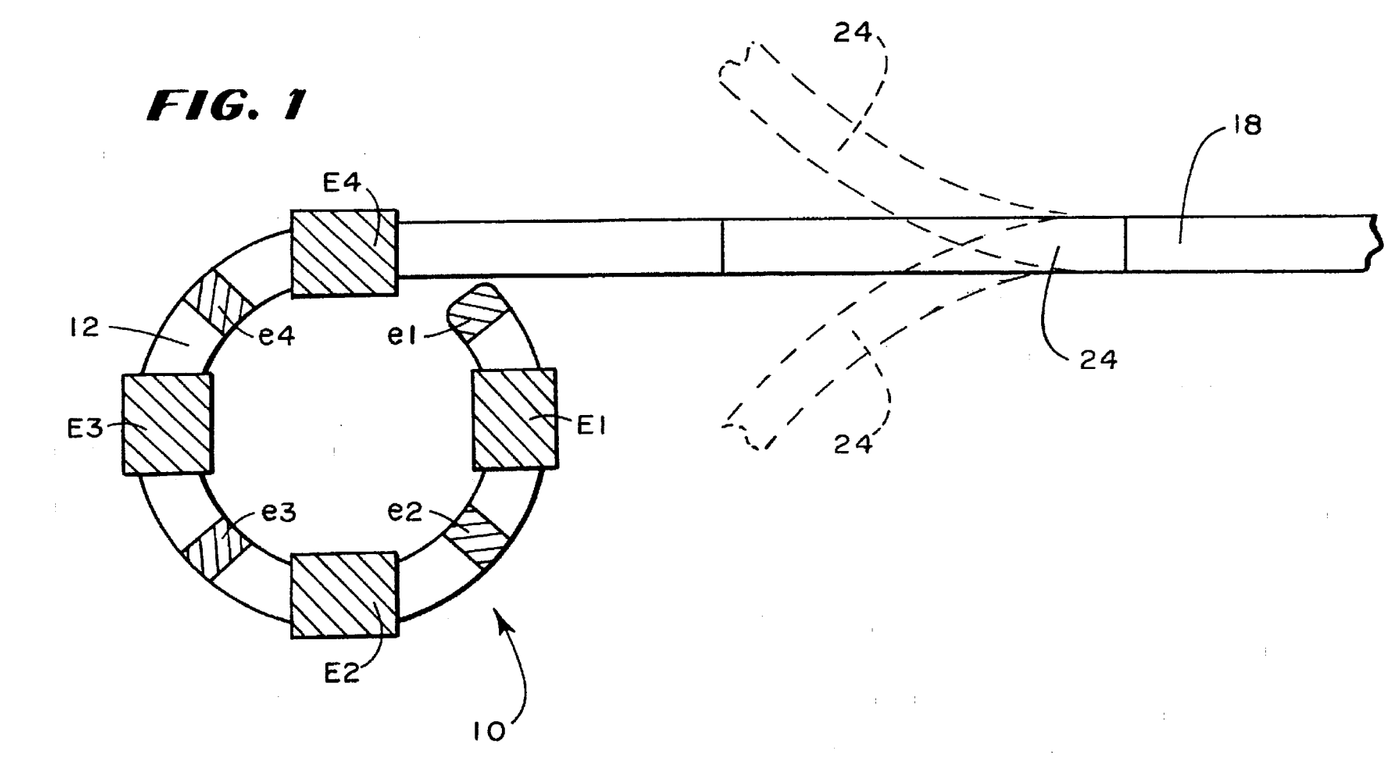
FIG. 1 is a multiple function element for mapping and ablating interior regions of the heart.

FIG. 1 shows a multiple function element 10 that locates and ablates arrhythmogenic foci in the heart.

The element 10 comprises an elongated body 12 that is preformed into a generally circular curved shape that resembles a loop.

The body 12 is preferably formed of an inert, resilient plastic material which retains its shape and does not soften significantly at body temperature, like Pebax®, polyethylene, or Hytrel® (polyester).

The geometry of the body 12 can be created by thermo-forming it into the desired shape. Alternatively, the body 12 can include an interior core of super-elastic material, like Nitinol wire, that is itself preshaped into the desired configuration.

This provides the element 10 with a modulus that lends both resilience and mechanical strength. As a consequence, the element 10 can be manipulated to make stable and uniform contact with tissue within the heart.

The body 12 carries a first array of ring electrodes (designated e1 to e4 in FIG. 1) aligned side by side along the axis of the body 12. The first electrode array e1 to e4 can also include an electrode on the distal tip of the body 12, as FIG. 1 shows.

Each ring electrode e1 to e4 in the first array is about 0.5 to 1.5 mm in length.

The body 12 also carries a second array of ring electrodes (designated E1 to E4 in FIG. 1) aligned side by side along the axis of the body 12 in between the electrodes e1 to e4 of the first array.

The ring electrodes E1 to E4 in the second array are larger than the ring electrodes e1 to e4 in the first array. Each ring electrode E1 to E4 in the second array is about 2 mm to 5 mm in length.

The particular number, spacing, and dimensions of the electrodes e1 to e4 and E1 to E4 in each array can of course vary according to the particular geometry and functionality desired. The loop diameter of the body 12 and electrode placement can vary, depending upon the desired lesion size and power output selected.

In the illustrated embodiment, the loop body 12 is about 1 to 2.5 cm in diameter, with the distal-most curve having a tight radius (e.g., less than about 1.5 cm). The loop body 12 carries a total of eight electrodes, which are approximately equally spaced radially about the loop shape. The four smaller electrodes e1 to e4 comprise the first array, and the four larger electrodes E1 to E4 comprise the second array.

According to the invention, the first array of smaller electrodes e1 to e4 and the second array of larger electrodes E1 to E4 serve together to map and locate arrhythmogenic foci. The second array of larger electrodes E1 to E4 also serves by itself to ablate the foci, once located. In the illustrated and preferred embodiment, the electrodes e1 to e4 in the first array are not used for ablation. According to the invention, large lesions are created using the larger electrodes E1 to E4.

The ring electrodes e1 to e4 and E1 to E4 in the arrays can be made of a solid, electrically conducting material, like platinum or gold, attached about the body. Alternatively, the ring electrodes e1 to e4 and E1 to E4 can be formed by coating the exterior surface of the body 12 with an electrically conducting material, like platinum or gold. The coating can be applied using sputtering, ion beam deposition, or equivalent techniques.

According to the invention, the element 12 is part of an overall system 14 (see FIG. 2) that delivers, deploys, and operates the element 10 inside the heart.

Figure 2:
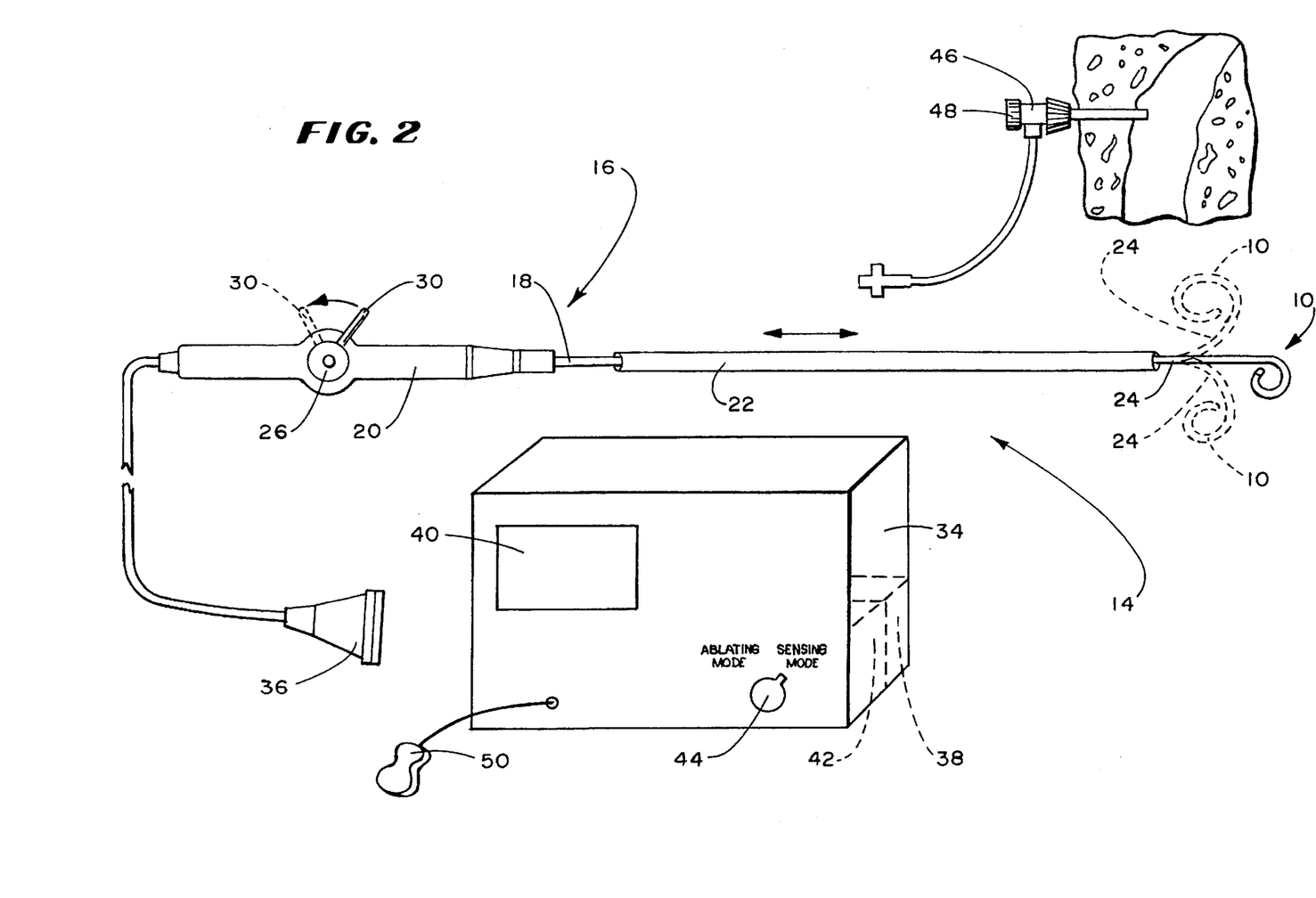
FIG. 2 is a system for introducing, deploying and using the element shown in FIG. 1 to map and ablate interior regions of the heart.

As FIG. 2 shows, the system 14 includes a probe 16. The probe 16 has a guide tube 18 that carries the element 10 at its distal end (see FIG. 1 also). The probe 16 also includes a handle or grip 20 attached to the proximal end of the guide tube 18. The guide tube 18 carries a guide sheath 22, which slides fore and aft along the axis of the guide tube 18.

Figures 3, 4:
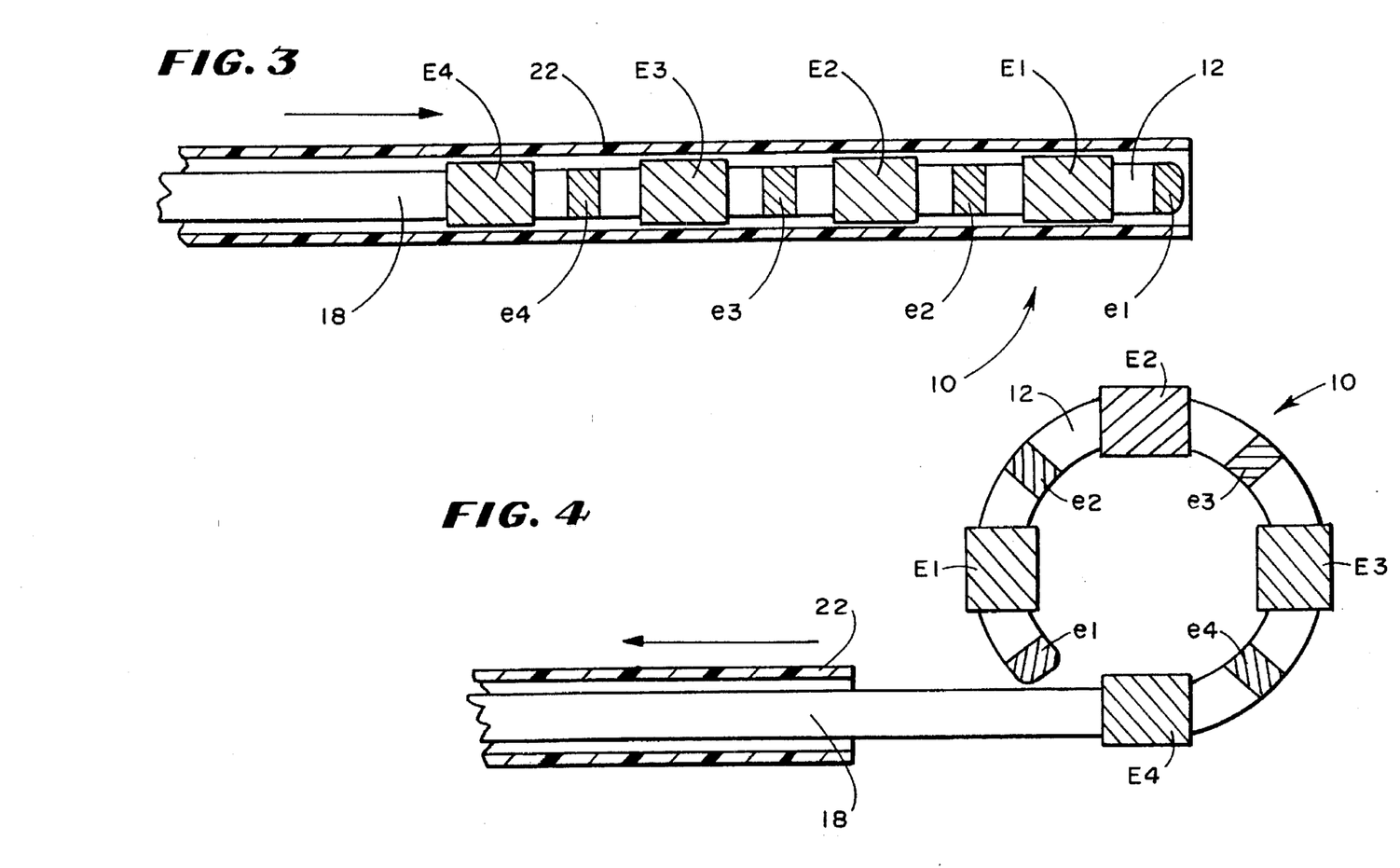
FIG. 3 is a side section view of a movable guide sheath used to shape the element, with the guide sheath moved forward to straighten and enclose the element.
FIG. 4 is a side section view of the movable guide sheath shown in FIG. 3, moved rearward to deploy the element for use.

As FIG. 3 shows, sliding the guide sheath 22 forward (that is, toward the element 10), progressive straightens out the resilient body 12 while drawing it into the guide sheath 22.

As FIG. 3 also shows, when confined within the guide sheath 22, the body 12 assumes the generally linear, low profile shape of the guide sheath 22. The low profile shape allows the physician to employ conventional percutaneous access techniques to introduce the element 10 into a selected region of the heart through a vein or artery.

As FIG. 4 shows, sliding the guide sheath 22 to the rear (that is, away from the element 10), frees the body 12 from the confines of the sheath 22. The resilient memory of the body 12 causes it to return to its preformed shape, as FIG. 4 shows.

In the illustrated and preferred embodiment, a distal section 24 of the guide tube 18 (see FIG. 1) adjacent the element 10 can be remotely flexed or steered by the physician, as shown in phantom lines in FIG. 1. As shown in FIG. 2, by flexing the distal section 24, the physician steers the element 10. The handle 20 encloses a steering mechanism 26 for the distal section 24.

The steering mechanism 26 can vary. In the illustrated embodiment (see FIG. 5), the steering mechanism is the one shown in U.S. application Ser. No. 07/789,260, now U.S. Pat. No. 5,363,861 issued Nov. 15, 1994 which is incorporated by reference.

Figure 5:
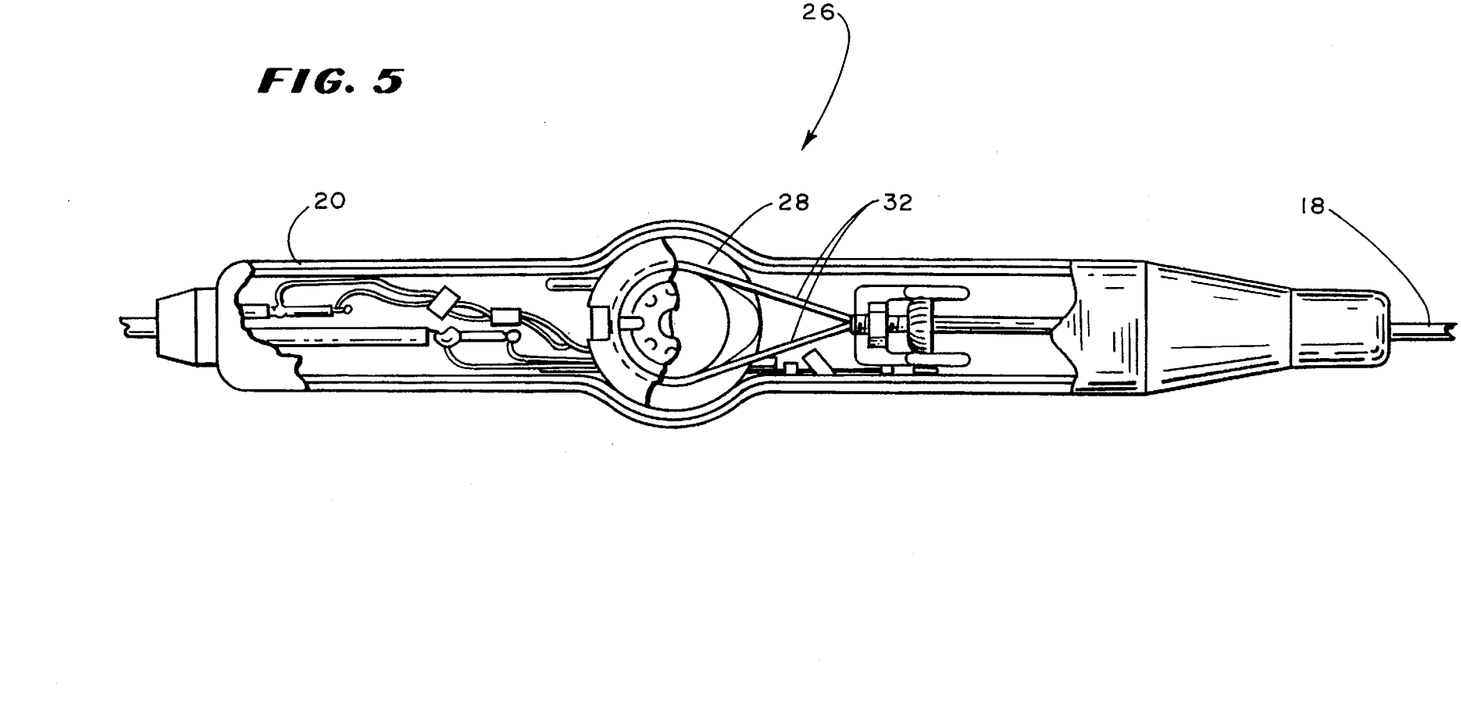
FIG. 5 is a top view, with portions removed and in section, a steering mechanism that can be used to remotely steer the element.

As FIG. 5 shows, the steering mechanism 26 of this construction includes a rotating cam wheel 28 within the handle 20. An external steering lever 30 rotates the cam wheel 28. The cam wheel 28 holds the proximal ends of right and left steering wires 32.

The steering wires 32 extend along the associated left and right side surfaces of the cam wheel 28 and through the guide tube 18. The steering wires 32 connect to the left and right sides of a resilient bendable wire or spring (not shown) within the distal section 24.

As FIG. 2 shows, forward movement of the steering lever 30 bends the distal section 24 and element 10 down. Rearward movement of the steering lever 30 bends the distal section and element 10 up. By rotating the, handle 20, thereby rotating the element 10, and thereafter manipulating the steering lever 30 as required, it is possible to maneuver the element 10 virtually in any direction. The steerable section 24 simplifies the positioning of the multiple purpose element 10 within the heart.

As FIG. 2 also shows, the system 14 also includes a controller 34. Each ring electrode e1 to e4 and E1 to E4 is electrically coupled to a signal wire (not shown) made of an electrically conductive material, like copper alloy. The signal wires extend through the guide tube 18 into the handle 20. One or more connectors 36 attach the proximal ends of the signal wires to an input plug on the controller 34.

The controller 34 includes a signal monitor module 38. The signal monitor module 38 receives electrical signals detected by the ring electrodes e1 to e4 and E1 to E4 in the first and second arrays. The signal monitor module 38 processes the electrical signals to assist the physician in locating the arrhythmogenic focus.

In the illustrated and preferred embodiment, the signal monitor module 38 also includes a display device 40. The display device 40 presents an analysis of electrical activity in a format that the physician can readily view and interpret.

The controller also includes an energy generator module 42 that creates and transmits radiofrequency electromagnetic energy to the ring electrodes E1 to E4 of the second array. The ring electrodes E1 to E4 emit the energy to ablate myocardial tissue.

In the illustrated and preferred embodiment, the generator module 42 operates to apply ablating energy to the ring electrodes E1 to E4 in a bipolar mode.

The controller also includes a switch 44 for selecting either the signal monitor module 38 or the energy generator module 42, thereby choosing between operating the element 10 in a SENSING MODE and an ABLATING MODE.

To deploy the element 10 within the heart, the physician uses a conventional introducer 46 (see FIG. 2) to establish access to a selected vein or artery.

With the guide sheath 22 moved forward and enclosing the element 10 (as FIG. 3 shows), the physician introduces the outer sheath through a conventional hemostatic valve 48 on the introducer 46. The physician progressively advances the guide sheath 22 and guide tube 18 through the access vein or artery into the desired location in the heart.

The physician observes the progress of the outer sheath using fluoroscopic or ultrasound imaging, or the like. The guide sheath 22 can include a radio-opaque compound, such as barium, for this purpose. Alternatively, a radio-opaque marker can be placed at the distal end of the guide sheath 22.

The guide sheath 22 can itself be preshaped with a memory that assumes a prescribed curvature for simplifying access through arterial access.

Once located in the desired location within the heart, the physician slides the guide sheath 22 back to free the element 10, as FIG. 4 shows. The element 10 resiliently springs into its curved shape.

The physician can use fluoroscopic or ultrasound imaging, or the like, to observe the element 10 while maneuvering it using the steering mechanism 26 into good contact with endocardial tissue. Alternatively, the physician can deploy an angioscopic or ultrasonic viewing probe into the heart to aid positioning.

Once the physician obtains good contact between the element 10 and the endocardium in the selected area, the physician takes steps to map the area.

Operating the switch 44, the physician selects SENSING MODE on the controller 34. This activates the signal monitor module 38 and its associated display 40.

The signal monitor module 38 receives signals from the electrodes e1 to e4 and E1 to E4 of the first and second arrays. These signals reflect a particular electrical event in the cardiac cycle. More particularly, the signal monitor module 38 converts the receipt of the event by the individual electrodes in time to graphical information that allows the physician to "home in" upon the arrhythmogenic focus.

The module 38 can include a conventional microprocessor (e.g., with a 386/486 motherboard) to analyze the signals and converts them to graphic images on the display 40.

The nature and character of the graphic images on the display 40 can vary. In the illustrated and preferred embodiment (as FIG. 6 shows) the display 40 presents an array of graphic characters or icons (designated I1 to I8), equal in number to the total number of electrodes e1 to e4 and E1 to E4 carried on the element 10.

Figure 6:
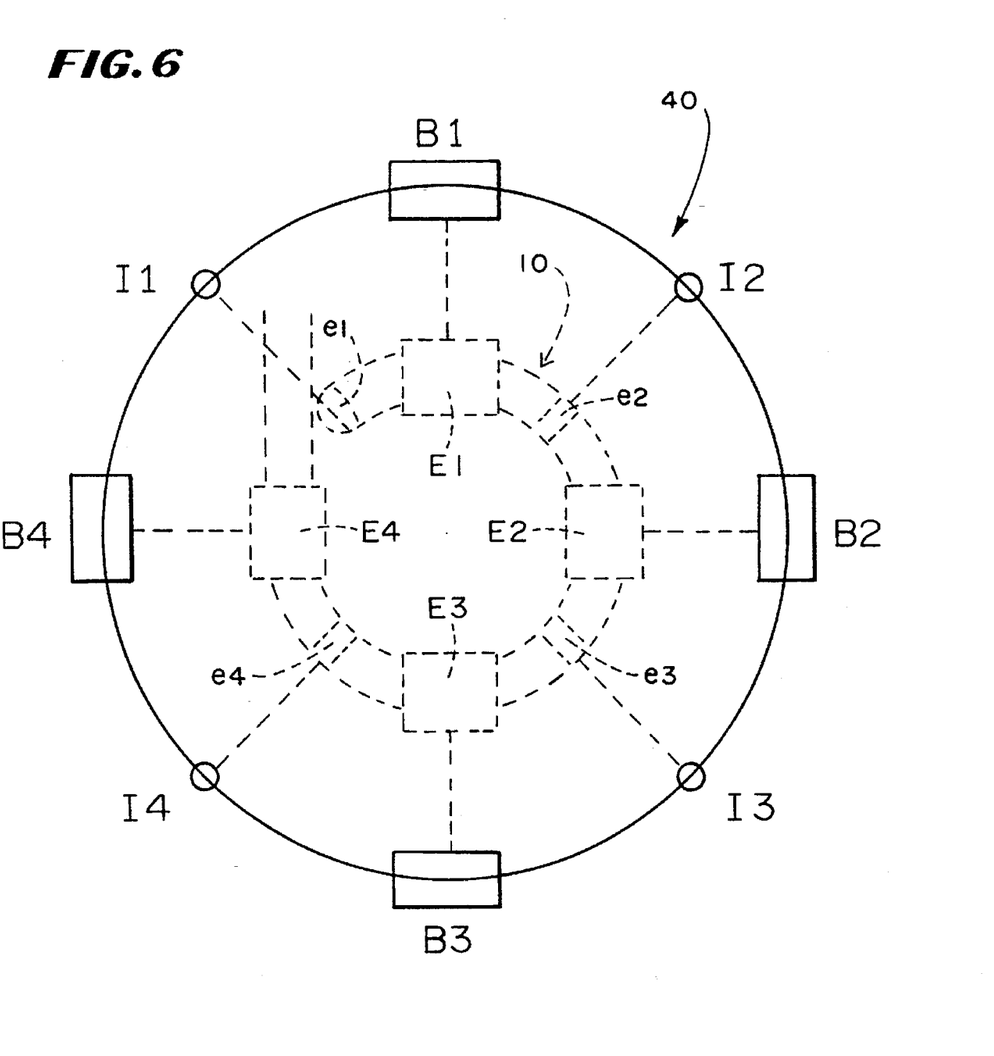
FIG. 6 is a view of the mapping display the system shown in FIG. 2 generates in use with the element shown in FIG. 1.

As shown in FIG. 6, the display 40 depicts the "footprint" of the loop body 12 of the element 10 (which is shown superimposed upon the display 40 in phantom lines).

In the illustrated display, the graphic characters take the shape of boxes (B1; B2; B3; and B4) and circles (I1; I2; I3; and I4). The boxes B1; B2; B3; and B4 correspond with the electrodes E1 to E4, as counted from the distal tip of the element 10. The circles I1 to I4 correspond with the electrodes e1 to e4 in the same fashion.

A conventional CRT can present the display 40. Alternatively, the display 40 can be presented on an LCD screen, or as a series of small lights or LCD's.

Preferably, the controller 34 includes an input device 50 for entering commands. In the illustrated embodiment, the input device 50 comprises a mouse, and the display 40 provides an interface that integrates input and output by accepting mouse-driven input from the display. However, other conventional input devices can be used, like a touch screen, key board, push button, or a voice activated input.

According to another aspect of the invention, the individual icons B1 to B4 and I1 to I4 display within themselves graphic information that represents the time sequence in which the associated ring electrodes detect the particular electrical event. This time sequence is derived by the signal module 38 and converted to graphical information.

In the illustrated and preferred embodiment, the sequence is ordered by time-gating. Time gating identifies the first electrode to receive the electrical event. It then orders the later receipt of the electrical events according to electrode groups that receive later electrical events within prescribed time gates following the initial receipt.

In the preferred embodiment, the graphic information is displayed as colors within the icons B1 to B4 and I1 to I4.

More particularly, the sensing module 38 displays a selected first color C1 in the icon corresponding to the electrode that first receives the electrical event. The module 38 displays a second color C2 in the icons corresponding to the electrodes that receive the event in the first time gate; a third color C3 in the icons corresponding to the electrodes that receive the event in the next time gate; and so on.

For example, the sensing system can cause the first receiving electrode box to display the color red. The subsequent electrode boxes sequentially fade using different colors (or different shades of the same color) from red to yellow and eventually to blue. The colors displayed in the boxes visually guide the physician to the site of the arrhythmogenic focus.

Figure 7A:
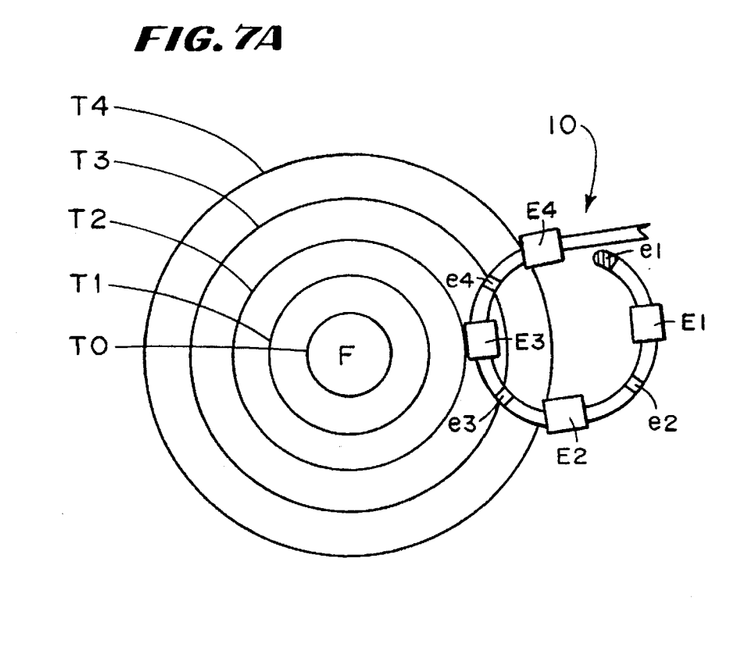
FIG. 7A is a diagrammatic view of the element shown in FIG. 1 located within the heart at a position spaced from an arrhythmogenic focus.

FIG. 7A diagrammatically shows the propagation of an electrical event as waves of heart cell depolarization and subsequent repolarization that spread during successive time intervals T1 to T4 from an arrhythmogenic focus F across the endocardium. FIG. 7A, also shows the element 10 at a first location spaced from the focus.

Figure 7B:
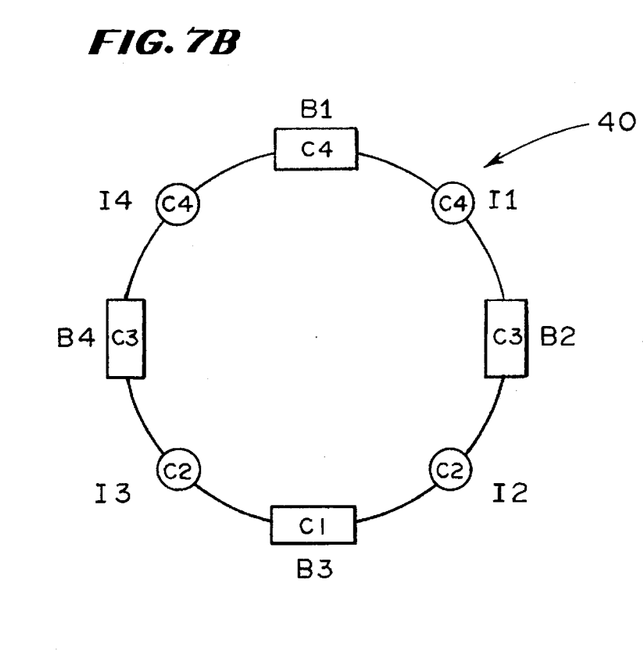
FIG. 7B is a view of the mapping display generated when the element is positioned as shown in FIG. 7A.

FIG. 7B shows the corresponding display 40. As FIG. 7B shows, electrode E3 first senses the electrical event at T2, and therefore displays the first color C1 in icon B3. In the next time gate (from T2 to T3), electrodes e3 and e4 next sense the event, and therefore display the second color C2 in icons I2 and I3. In the next time gate (from T3 to T4), electrodes E2 and E4 sense the event, and therefore display the third color C3 in icons B2 and B4. Electrodes E1, e1, and e2 will sense the event in the next time gate (T4 to T5, not shown), and will therefore display the fourth color C4 in icons B1, I1, and I4.

As FIG. 7B shows, when the element 10 is spaced from the focus F, there is a marked variation in colors displayed in the icons (i.e., from C1 to C4).

The time gate sequence derived by the module 38 enables the physician to "home in" upon the focus F. More particularly, by identifying the electrode (or electrodes) that first receive the event, the time gate sequence also identifies the direction in which the element 10 must be moved to reach the focus F. The physician must move the element in the direction of the electrode displaying the first color C1, until all electrodes in the element 10 display the same first color C1. At this time, the center of the element 10 registers with the focus F.

Figure 8A:
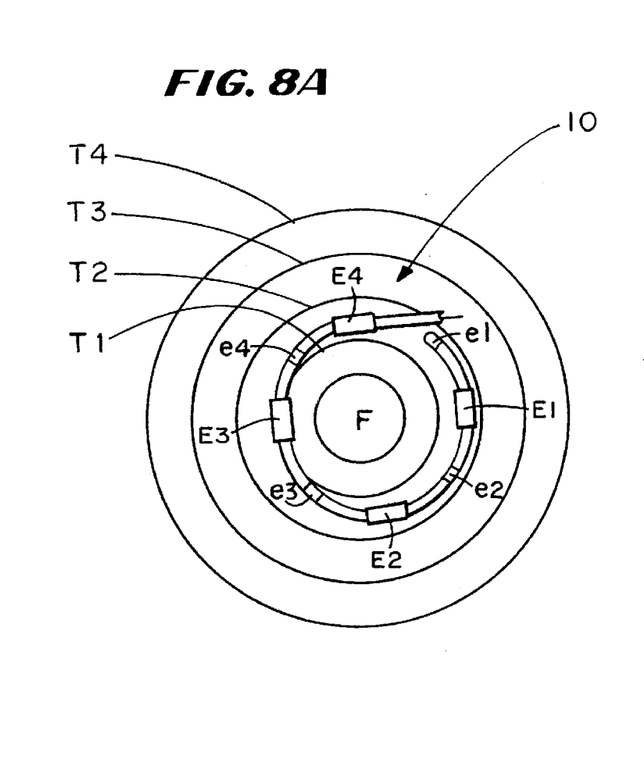
FIG. 8A is a diagrammatic view of the element shown in FIG. 1 located within the heart at a position closer to the arrhythmogenic focus than shown in FIG. 7A.
Figure 8B:
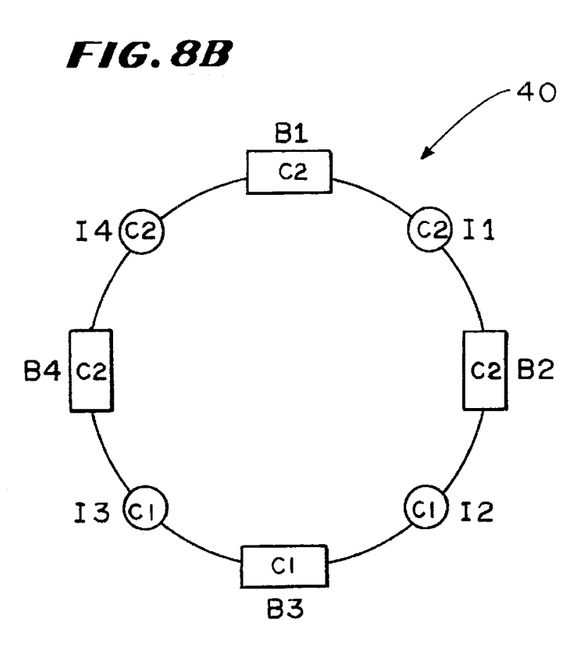
FIG. 8B is a view of the mapping display generated when the element is positioned as shown in FIG. 8A.

As FIG. 8A shows, the physician has moved the element 10 toward the first color electrode E3 (i.e., toward the left in FIG. 8A) to "home in" on the focus F. As FIG. 8B shows, the variation in colors in the display 40 becomes progressively less as the element 10 gets progressively closer to the focus F. The electrodes E3, e3, and e4 first receive the event essentially at the same time, and therefore display the first color c1 in icons B3, I2, and I3. All remaining electrodes receive the signal in the next time gate, and therefore all remaining icons B1, B2, B4 I1, and I4 commonly display the second color C2. That is, as the electrodes receive the event within fewer time gates, fewer colors are displayed.

Figure 9A:
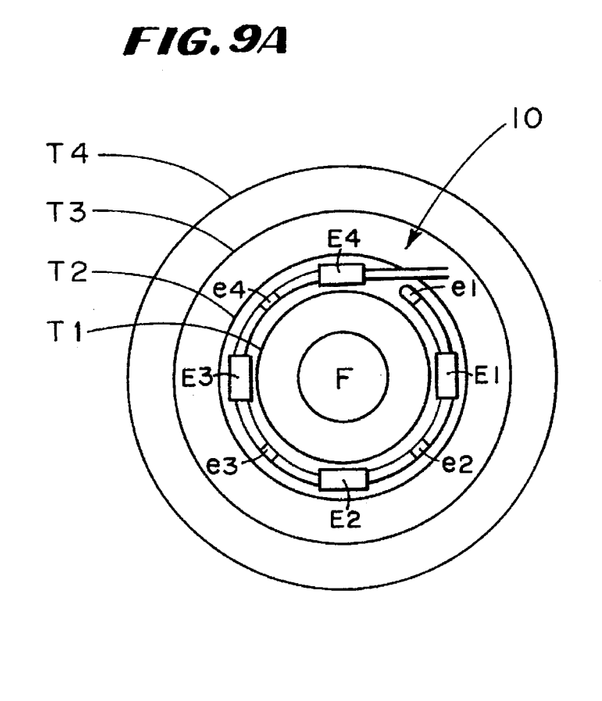
FIG. 9A is a diagrammatic view of the element shown in FIG. 1 located within the heart at a position centered about the arrhythmogenic focus shown in FIG. 7A.

FIG. 9A shows the element 10 moved further toward the first color electrode E3 (i.e., further to the left in FIG. 9A) so that its center is on or nearer to the focus F. All electrodes E1 to E4 and e1 to e4 receive the electrical event at nearly the same time. All icons on the display 40 show the same first color C1, as FIG. 9B shows.

Figure 9B:
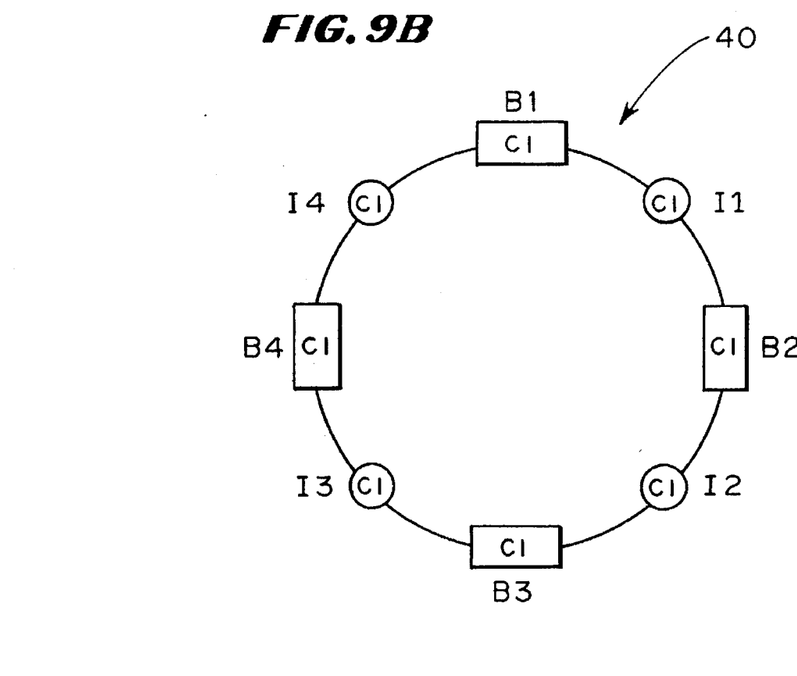
FIG. 9B is a view of the mapping display generated when the element is positioned as shown in FIG. 9A.

The display 40 in FIG. 9B indicates to the physician that it is time to begin the ablution process.

Instead on the continuous display 40, the signal monitor module 38 can be actuated by the physician to create a display of information acquired over a predetermined time period. In this arrangement, the physician would activate a switch, which would call upon the module 38 to compute and display the time gate sequence over the predetermined time period. After moving the element 10 based upon this display, the physician would activate the switch again, and the module 38 would compute another time gate sequence, updating the display. The physician would call for these update displays as required to complete the positioning of the element 10.

With the display, the physician does not have to know the absolute location of the electrodes e1 to e4 and E1 to E4 or the arrhythmogenic focus F itself. The invention allows the physician to proceed to ablate the focus F without pinpointing its exact coordinates within the heart.

The time gating methodology just discussed is based upon a relative time reference that begins when the first electrode receives the event and relates later receipt by other electrodes to this. Alternatively, the time gate could be based upon a real time reference generated from an external source, like a surface ECG signal or an electrogram obtained from a stationary catheter external to the element 10.

A real time reference allows the physician to relate the timing of the local electrogram sensed by the element to the real time reference, and thereby also identify an appropriate ablation site. For example, using the surface ECG signal as the time reference in relation to the local electrogram sensed by the element 10, the physician can identify the earliest depolarization site in the heart, which often is associated with an appropriate lesion site.

Figures 10A, 10B:
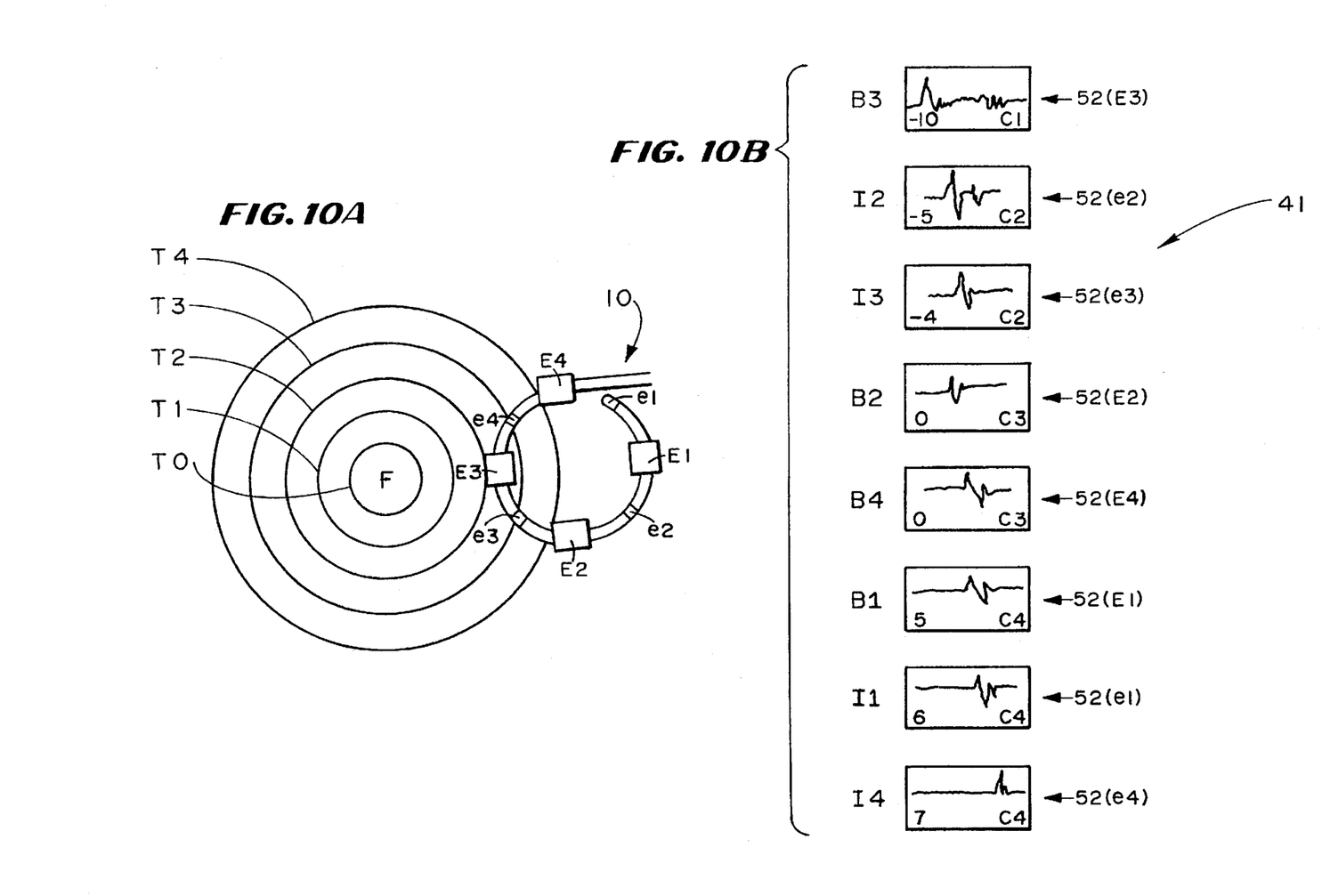
FIG. 10A is a diagrammatic view of the element shown in FIG. 1 located within the heart at a position spaced from an arrhythmogenic focus.
FIG. 10B is a view of an alternative mapping display that includes electrogram morphologies generated when the element is positioned as shown in FIG. 10A.

Alternatively, the display can integrate electrogram recordings made by the various electrodes E1 to E4 and e1 to e4 on the element 10. FIG. 10A shows the element 10 in generally the same location relative to the focus F as FIG. 7A. The alternative display 41 shows the individual electrogram signals recorded by the individual electrodes on the element 10 (designated as 52 (E1 to E4) and 52 (e1 to e4)), arranged from top to bottom according to time that the electrodes receive the event.

The electrogram signals 52 (E1 to E4/e1 to e4) can be displayed in the colors according to the time gate color code assigned to the display 40 shown in FIG. 7B. That is, the electrogram signal 52 (E3) of the first electrode E3 receiving the event could be displayed in color C1; the electrogram signals of the next electrodes e2 and e3 receiving the event could be displayed in color C2, and so on.

Alternatively, or in addition to the display of the time gate colors C1 to C4, the display 41 could include a number (shown in the lower left hand corner of the electrogram signal display in FIG. 10B) representing the time of receipt of the signal relative to a real time reference.

By showing electrogram signal morphology from each electrode on the element 10, the display 41 can be used to confirm the time gate analysis made by the signal monitor module 38. The electrogram signal morphology can be used by the physician to confirm the identity of the region where reentry occurs. For example, in FIG. 10B, the electrogram signal 52 (E3) (selected as a possible reentry pathway by the time gate analysis) also shows diastolic potentials (designated DP), further indicating close proximity to a re-entrant pathway (where local depolarization occurs in "diastole").

Operating the switch 44, the physician selects ABLATING MODE on the controller 34. This readies the energy generator module 42. The physician can then, upon additional commands, supply ablation energy to the element 10.

Figure 11:
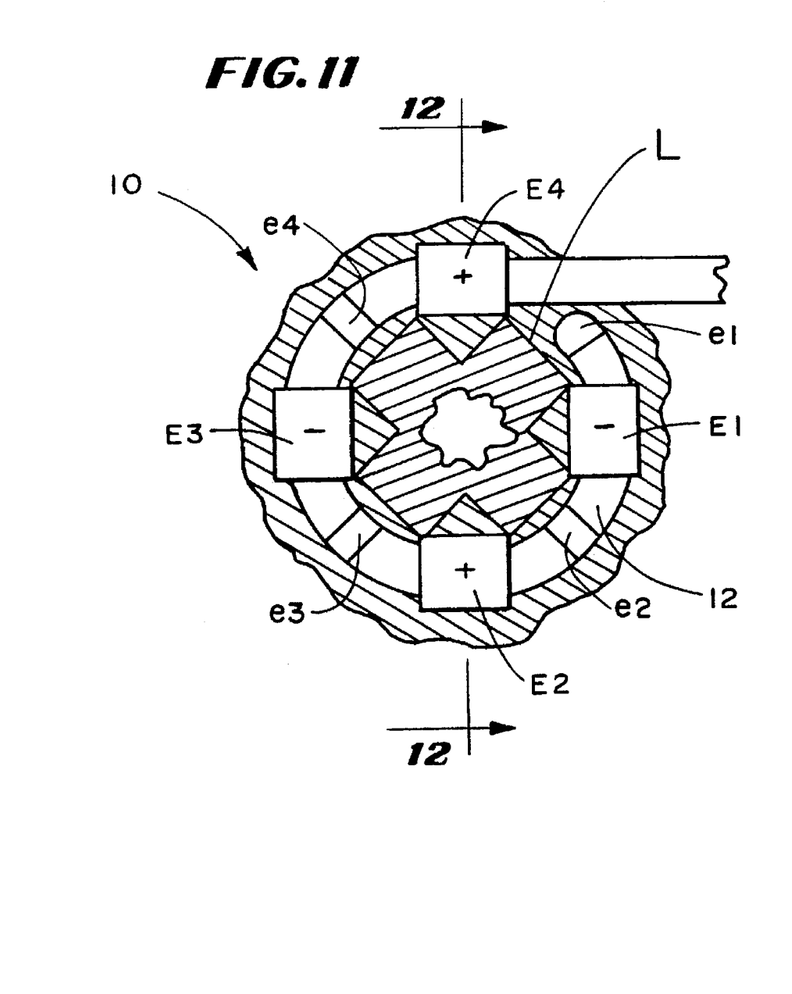
FIG. 11 is a somewhat diagrammatic top view of a lesion formed by the element shown in FIG. 1, when operated in a bipolar mode.

The module 42 operates in a bipolar mode to set the polarity of electrodes E1 to E4 in the second array to deliver radiofrequency energy between electrodes E1/E2; E2/E3; E3/E4; and E4/E1 (as FIG. 11 shows). The bipolar ablation sequence can be accomplished in various fashions, including sequential burns, phase offsets, or differing voltages from electrode to electrode. The controller 34 can employ automated, microprocessor controlled voltage switching among the electrodes E1 to E4 of the second array to achieved the desired bipolar ablation result.

Figure 12:
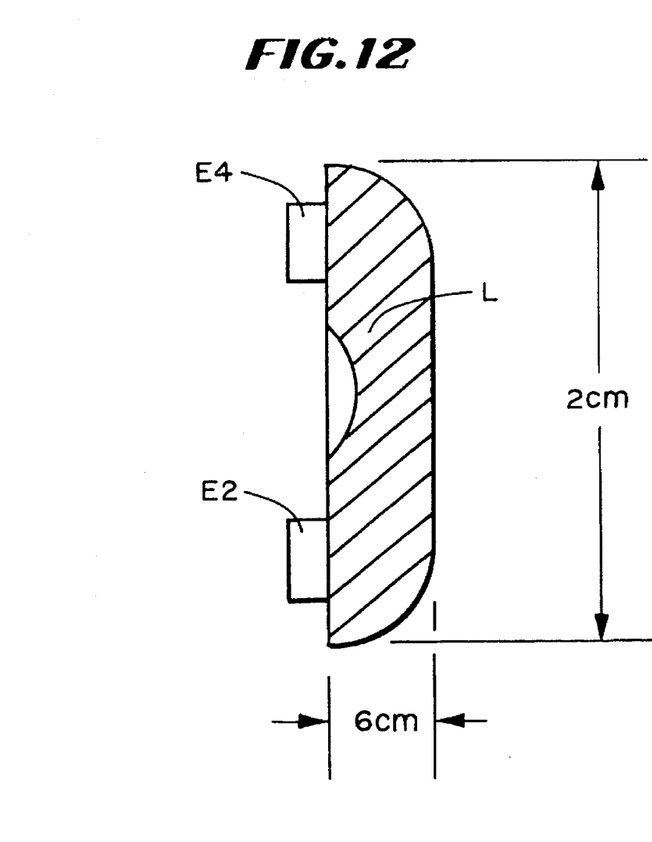
FIG. 12 is a somewhat diagrammatic side section view of the lesion formed by the element, taken generally along line 12—12 in FIG. 11.

As a result, a large lesion L forms occupying within and several millimeters beyond the loop body 12, as FIGS. 11 and 12 show. The lesion L is observed to also bow further outward in the region of the ablation electrodes E1, E2, E3, and E4. A typical lesion L formed by the element 10 measures in diameter about 6 mm more than the outer diameter of the element 10. The lesion L extends to a depth up to about 1 cm, depending upon the power applied. It has been observed that the application of about 40 watts of ablating energy in a bipolar mode results in a 1 cm lesion depth.

Using the switch 44, the physician can successively toggle between the SENSING MODE and the ABLATING MODE until the elimination of the focus has been confirmed.

The physician then slides the guide sheath 22 forward to enclose the element 10. The physician then withdraws the guide tube 18 and guide sheath 22 from the heart, ending the procedure.

In an alternative embodiment (not shown) conventional catheter steering technology can be used to shape the element 10. In this arrangement, the element 10 could be selectively bent or flexed without using the guide sheath 22 from a generally straight configuration to the desired curved configuration. A mechanism in the handle 20 could be used to remotely bend or flex the element 10 for this purpose.

Other alternative embodiments of the element would also not require an guide sheath 22. One alternative embodiment (not shown) includes the use of "shape memory" material that would change the shape of the element 10 upon exposure to the temperature conditions present in the heart. Another alternative embodiment would include an internal sliding styler to shape the element 10, as disclosed in patent application Ser. No. 08/99,843 filed Jul. 30, 1993, now U.S. Pat. No. 5,397,321 issued Mar. 14, 1995. In still another alternative embodiment, the element 10 itself may possess sufficient inherent flexibility to permit its advancement through the vasculature without a guide sheath 22.

Nevertheless, use of the sliding guide sheath 22 is preferred, because it allows the element 10 to be made with enough inherent stiffness to generate greater contact forces with the tissue.

According to the invention, the selected arrhythmogenic focus can be mapped and ablated at one time, without the need to employ a separate ablation probe. The invention provides better tissue/electrode contact and stability, to minimize the occurrence of ineffective applications of ablating energy. Furthermore, the invention provides lesions of enlarged size. The invention thereby provides shorter and more effective procedures, with greater incidence of curative lesions.

The features of the invention are set forth in the following claims.

We claim:

1. An assembly for sensing electrical events and forming lesions in heart tissue by means of bipolar electrodes comprising a support body for contacting heart tissue, the body having an elongated manipulatable shape for insertion into a heart chamber through a blood vessel and being formable after insertion therein into a generally circular shape defining an open interior region and adapted to encircle an area adjacent to the surface of the heart tissue contacted, an array of first electrodes positioned in a spaced apart pattern on the support body about the open interior region, the first electrodes having a first length, an array of second electrodes positioned in a spaced apart pattern on the support body about the open interior region, the second electrodes being grouped in bipolar pairs with electrodes of the same polarity being positioned diametrically opposite each other across the open interior region, the second electrodes having a second length substantially larger than the first length, signal wires electrically coupled to the first and second electrodes and being operative (i) in a first mode for conveying signals representing electrical events sensed by both the first and second electrodes when in contact with heart tissue, and (ii) in a second mode for conveying ablating energy only to the bipolar pairs of the second electrodes and not to the first electrodes to form a bipolar lesion in the heart tissue enclosed within the open interior region of the support body.

2. An assembly according to claim 1 wherein the first electrodes comprise ring electrodes that encircle the support body.

3. An assembly according to claim 1
wherein the second electrodes comprise ring electrodes that encircle the support body.

4. An assembly according to claim 1 wherein both the first and second electrodes comprise ring electrodes that encircle the support body.

5. An assembly according to claim 1
wherein the spaced apart patterns of the arrays sequentially locate one of the first electrodes next to one of the second electrodes along the support body.

6. An assembly according to claim 1
wherein the first physical dimension ranges in length between about 0.5 mm to 1.5 mm, and wherein the second physical dimension ranges in length 2 mm to 5 mm.

7. An assembly according to claim 1
wherein at least some of the first and second electrodes comprise a metallic element made of electrically conducting material.

8. An assembly according to claim 1
wherein at least some of the first and second electrodes comprise an electrically conducting coating applied upon the support body.

9. A catheter for sensing electrical activity and ablating tissue in heart tissue comprising a guide body having a distal end, an electrode array carried on the distal end of the guide body including a support body for contacting heart tissue, the body having an elongated manipulatable shape for insertion into a heart chamber through a blood vessel and being formable after insertion therein into a generally circular shape defining an open interior region adapted to encircle an area adjacent to the surface of the heart tissue contacted, an array of first electrodes positioned in a spaced apart pattern on the support body about the open interior region, the first electrodes having a first length, and an array of second electrodes positioned in a spaced apart pattern on the support body about the open interior region, the second electrodes being grouped in bipolar pairs with electrodes of the same polarity being positioned diametrically opposite each other across the open interior region, the second electrodes having a second length larger than the first length, and signal wires electrically coupled to the first and second electrodes and being operative (i) in a first mode for conveying signals representing electrical events sensed by both the first and second electrodes when in contact with heart tissue, and (ii) in a second mode for conveying ablating energy only to the bipolar pairs of the second electrodes and not to the first electrodes to form a bipolar lesion in the heart tissue enclosed within the open interior region of the support body.

10. A catheter according to claim 9
wherein at least some of the first electrodes comprise ring electrodes that encircle the support body.

11. A catheter according to claim 9
wherein the spaced apart patterns of the arrays sequentially locate one of the first electrodes next to one of the second electrodes along the support body.

12. A catheter according to claim 9
wherein the first physical dimension ranges in length between about 0.5 mm to 1.5 mm, and wherein the second physical dimension ranges in length 2 mm to 5 mm.

13. An assembly according to claim 9
wherein at least some of the first and second electrodes comprise a metallic element made of electrically conducting material.

14. An assembly according to claim 9
wherein at least some of the first and second electrodes comprise an electrically conducting coating applied upon the support body.

15. A catheter according to claim 9
wherein the guide body includes a proximal end, and and further including a handle carried on the proximal end of the guide body for manipulating the guide body.

16. A catheter according to claim 9
and further including means for steering the distal end of the guide body.

17. A system for sensing electrical events in heart tissue comprising a catheter according to claim 9, and further comprising a signal monitor electrically coupled to the signal wires for conveying signals representing electrical events sensed by electrodes when in contact with heart tissue, the monitor including display means for displaying graphic information that represents the time sequence in which the electrodes on the support body sense a given electrical event.

18. A system according to claim 17
wherein the display means includes icons symbolizing the first and second electrodes.

19. A system according to claim 17
wherein the display means includes alpha-numeric characters that change according to the time sequence of sensing.

20. A system according to claim 17
wherein the display includes colors that change according to the time sequence of sensing.

21. A system according to claim 17
wherein the display shows electrogram recordings made by the electrodes.

22. A system according to claim 21
wherein the display orders the presentation of the electrogram recordings from first to last according to time sequence of sensing.

23. A system according to claim 17
wherein the controller includes means for time gating the sequence in which the electrodes sense the given electrical event.

24. A system according to claim 17
wherein the time sequence begins when the first one of the electrodes senses the given event.

25. A system according to claim
wherein the time sequence begins based upon a time reference initiated by an external source.

26. A system according to claim 17
wherein the controller includes means for conveying energy to one or more of the electrodes for ablating heart tissue.

* * * * *